US006258423B1

(12) United States Patent
Giori

(10) Patent No.: US 6,258,423 B1
(45) Date of Patent: Jul. 10, 2001

(54) MULTILAYER CHLORINE-FREE FILM WITH POLYESTER BARRIER LAYER AND OSTOMY POUCHES FORMED THEREFROM

(75) Inventor: Claudio Giori, Riverwood, IL (US)

(73) Assignee: Hollister Incorporated, Libertyville, IL (US)

(*) Notice: Subject to any disclaimer, the term of this patent is extended or adjusted under 35 U.S.C. 154(b) by 0 days.

(21) Appl. No.: 09/378,798

(22) Filed: Aug. 23, 1999

Related U.S. Application Data

(63) Continuation-in-part of application No. 09/083,800, filed on May 22, 1998, now abandoned.

(51) Int. Cl.[7] .............................. B29D 22/00; B32B 7/02; B32B 7/12; B32B 27/08; B32B 27/32
(52) U.S. Cl. .................. 428/36.7; 428/35.2; 428/36.7; 428/220; 428/347; 428/476.1; 428/522; 428/523
(58) Field of Search ................... 428/35.2, 35.7, 428/36.7, 220, 347, 200, 474.4, 475.8, 476.1, 476.3, 476.6, 476.9, 522, 523

(56) References Cited

U.S. PATENT DOCUMENTS

| 5,407,713 | 4/1995 | Wilfong et al. | 428/34.1 |
| 5,496,295 | 3/1996 | Wilfong et al. | 604/332 |
| 5,567,489 | 10/1996 | Allen et al. | 428/34.1 |
| 5,643,375 | 7/1997 | Wilfong et al. | 156/244.24 |
| 5,895,694 | 4/1999 | Zavadsky et al. | 428/36.7 |

FOREIGN PATENT DOCUMENTS

| 0 700 777A | 3/1996 | (EP) . |
| 0 787 580A | 8/1997 | (EP) . |

Primary Examiner—Harold Pyon
Assistant Examiner—Michael C. Miggins
(74) Attorney, Agent, or Firm—Marshall, O'Toole, Gerstein, Murray & Borun

(57) ABSTRACT

A multilayer heat-sealable chlorine-free film of relatively low modulus, high interlaminar strength, and low noise upon flexing is provided. The film comprises an odor barrier layer of polyester resin and at least one heat-sealable skin layer, preferably two such skin layers on opposite sides of said odor barrier layer, composed of a homopolymer of ethylene or a copolymer of ethylene and an alpha-olefin or an ester-containing monomer. In a preferred embodiment, the odor barrier layer is formed of polyethylene terephthalate and adhesive tie layers are interposed between the odor barrier layer and the skin layers, resulting in a multilayer film of five layers. Pouches formed of such multilayer films are also disclosed.

10 Claims, 1 Drawing Sheet

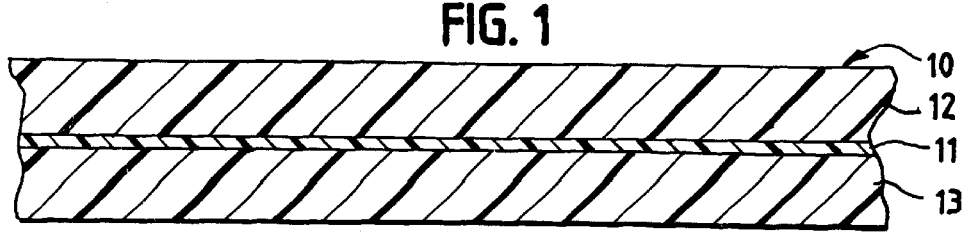
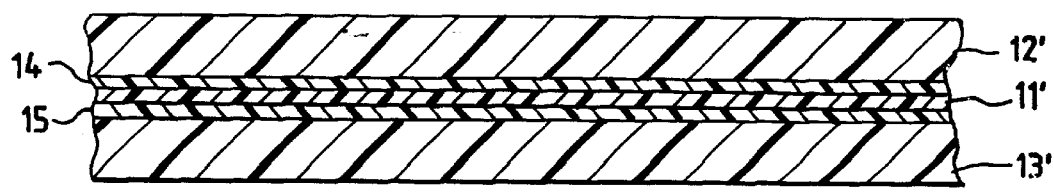
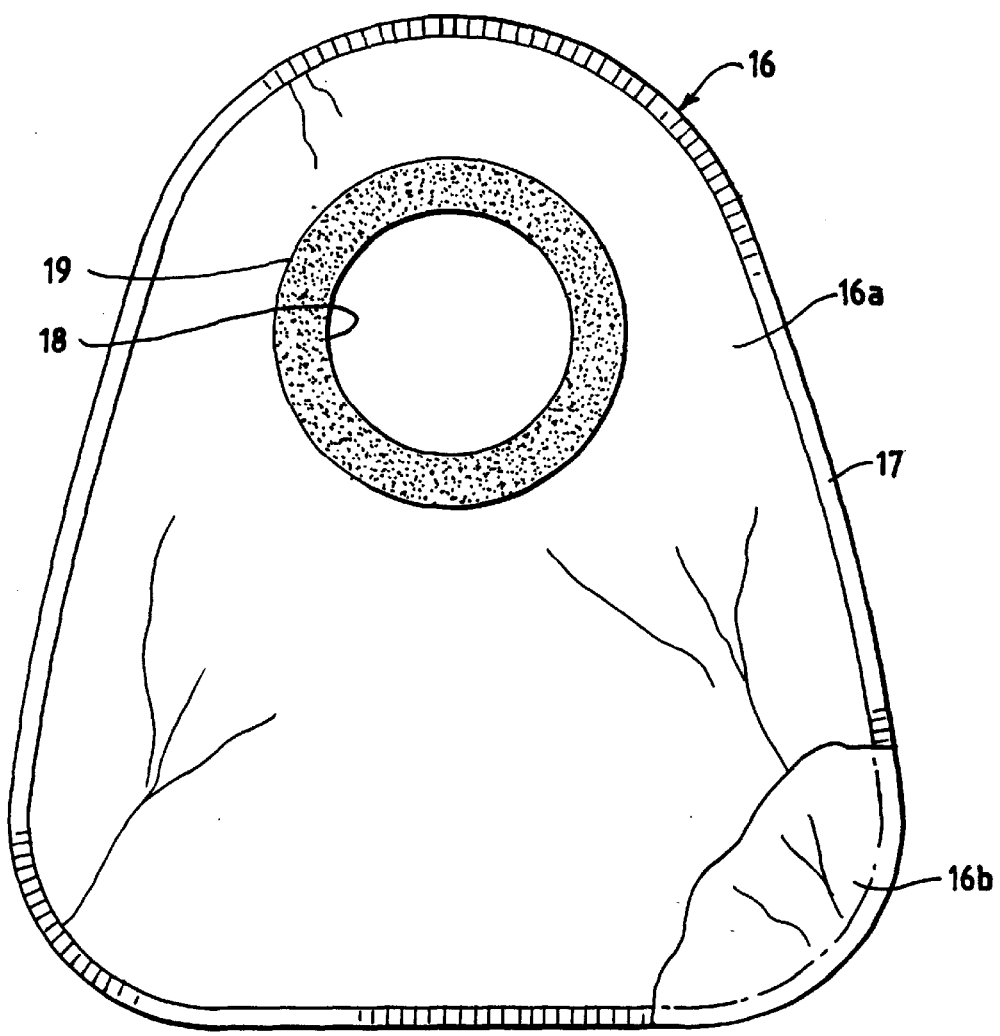

MULTILAYER CHLORINE-FREE FILM WITH POLYESTER BARRIER LAYER AND OSTOMY POUCHES FORMED THEREFROM

RELATED APPLICATION

This application is a continuation-in-part of my application Ser. No. 09/083,800, filed May 22, 1998, now abandoned.

BACKGROUND AND SUMMARY

Films for ostomy applications should have good odor barrier properties and produce minimal noise when flexed or wrinked to avoid embarrassment to users. Typically, films currently in use for ostomy applications utilize polyvinylidene chloride (PVDC) or copolymers of vinylidene chloride with a comonomer such as methylacrylate or vinylchloride as the gas barrier layer of a multilayer film. Such multilayer films have good resistance to odor transmission and are also relatively quiet; however, they are also believed to be hazardous to the environment when disposed of by incineration, a common practice in numerous countries. Chlorinated polymers generate hydrochloric acid as a byproduct of incineration and are believed to be a significant contributor to hydrochloric acid release from incinerator flue gases. Furthermore, chlorinated polymers are believed to form toxic dioxin derivatives as byproducts of incineration which are retained in the ashes and may possibly cause solid waste disposal problems.

Unfortunately, films formed of chlorine-free barrier resins tend to be stiffer and noisier than films utilizing conventional PVDC-based resins and do not match the quality of conventional chlorinated films for use in ostomy appliances. Thus, a need exists for a multilayer film which is chlorine-free, can be manufactured by coextrusion from readily available raw materials, is heat sealable, has high softness and low noise when flexed or wrinkled, and is impermeable to fecal odors.

U.S. Pat. No. 5,567,489 discloses a multilayer barrier film in which a chlorine-free barrier layer is composed of amorphous nylon, crystalline nylon, copolymers of ethylene and vinyl alcohol, or blends thereof. Although data presented in the patent indicate the multilayer films to be comparable in quietness to some chlorinated films in general commercial use, experience has revealed that such chlorine-free films are nevertheless significantly noisier than the chlorine-containing films commonly employed for the fabrication of ostomy pouches. The general observation is that chlorine-free barrier resins are high modulus, stiff materials that do not lend themselves to the production of low noise ostomy films. This is true of all nylon (polyamide) barrier resins, both crystalline and amorphous. It is true also of other known chlorine-free barrier resins such as hydrolyzed ethylene-vinylacetate copolymers, commonly known as ethylene-vinylalcohol copolymers, and copolymers of acrylontrile or methacrylontrile of high nitrile content, commonly known as nitrile resins.

Other references illustrating the current state of the art relating to chlorine-free multilayer films are U.S. Pat. Nos. 5,496,295, 5,643,375, and 5,407,713.

One aspect of this invention lies in the discovery that if a chlorine-free multilayer film is composed of polyester resin coextruded with at least one skin layer, preferably two such skin layers, of a homopolymer of ethylene or copolymer with alpha-olefin or ester-containing comonomer, the resulting multilayer film is of relatively low modulus and exhibits low noise upon flexing. The polyester resin barrier layer, although having limited oxygen permeability, is highly effective as an odor barrier, thereby resulting in a multilayer film particularly suitable for the fabrication of ostomy pouches. The polyester resin of choice is polyethylene terephthalate, and the skin layers are composed of a copolymer of ethylene and an ester-containing monomer such as methyl acrylate, ethyl acrylate, butyl acrylate or vinyl acetate. While the skin layers and barrier layer may be coextruded in direct contact with each other, it has been found that the interlaminar strength of the film may be significantly increased by interposing adhesive tie layers between the skin layers and barrier layer. Each such tie layer may be an ethylene copolymer with reactive functional groups, such as an anhydride modified copolymer of ethylene and an acrylic or methacrylic ester.

In addition to being heat-sealable and having exceptional odor-barrier properties, the multilayer films of this invention are relatively soft (have low modulus) and are superior in quietness to known chlorine-free films in which the odor-barrier layers are formed entirely of nylon, ethylene-vinylalcohol copolymers, or nitrile resins. With regard to the generation of noise upon flexing, the chlorine-free multilayer films of this invention compare favorably with prior art ostomy films having chlorinated barrier layers. A pouch formed of the multilayer film of this invention therefore has properties comparable to those exhibited by high-quality pouches formed of chlorine-containing compositions but without the environmental shortcomings described above.

Other features, advantages and objects of the invention will become apparent from the specification and drawings.

DRAWINGS

FIG. 1 is a schematic cross-sectional view of an embodiment of the multilayer barrier film of this invention.

FIG. 2 is a schematic cross-sectional view of a second embodiment of the multilayer barrier film of this invention.

FIG. 3 is an elevational view of an ostomy pouch formed from the multilayer film of FIGS. 1 or 2.

DETAILED DESCRIPTION OF PREFERRED EMBODIMENTS

The multilayer barrier film of the present invention may be produced using standard coextrusion techniques involving either casting or blowing. Preferably, the multilayer film includes three primary layers—a chlorine-free barrier layer sandwiched between two heat-sealable skin layers—but the advantages of the invention may be partially achieved in a structure having only two primary layers, that is, a barrier layer and a single skin layer. Also, as described hereinafter, while the skin layer(s) may be coextruded in direct contact with the barrier layer, optimum interlayer adhesion is achieved by interposing a suitable tie layer as an adhesion promoter between each barrier layer and skin layer, resulting in a preferred embodiment in which there are a total of five layers.

FIG. 1 schematically illustrates a multilayer barrier film 10 having a barrier layer 11 disposed between skin layers 12 and 13. The chlorine-free barrier layer 11 is composed of polyester resin. While various polyester resins are believed suitable, particularly effective results are achieved with polyethylene terephthalate resin. A toughened grade of polyethylene terephthalate such as Selar PTX184 commercially available from duPont Co. is suitable. Even though such a polyester resin is only a moderate barrier to oxygen and is inferior in oxgen barrier properties to conventional chlorinated barrier resins based on PVDC, it has been found to be an excellent barrier to simulated fecal odorants and is therefore especially useful for use in fabricating ostomy pouches. Because of its effectiveness as an odor barrier, a polyester layer having a thickness of only 0.2 mil has been found sufficient to provide excellent odor barrier properties. In general, the thickness of the barrier layer should fall within the range of 0.1 to 1.0 mil with the lower limit being established by the capability of the extrusion process and the upper limit by the physical properties contributed by the barrier layer in achieving a multilayer film having low modulus and low noise characteristics. Preferably, the barrier layer thickness should fall within the range of 0.1 to 0.4 mil, with 0.2 mil being considered optimal when factors such as odor barrier properties, softness, quietness, and ease of extrusion are all considered together.

Skin layers 12 and 13 are formed of an ethylene-based polymer or copolymer with an alpha-olefin such as hexene or octene or with an ester-containing comonomer such as methyl acrylate, ethyl acrylate, butyl acrylate, or vinyl acetate. A particularly effective skin layer composition suitable for coextrusion with barrier layer 11 is a copolymer of ethylene and methyl acrylate (EMA) having a methyl acrylate content in the range of about 10 to 30% by weight. A methyl acrylate content in the range of about 18 to 20% of the skin layer composition is believed optimal.

While the term "skin" is used to describe outer layers 12 and 13, such layers are in general considerably thicker than the barrier layer sandwiched between them. For example, each skin layer may have a thickness within the general range of 0.5 to 3 mil, preferably 1 to 2 mil, which may be nearly one order of magnitude greater than the thickness of the odor barrier layer 11. The skin layers provide strength, softness, and heat sealability for the multilayer film. EMA as the composition for the skin layer is preferred because of its softness and quietness, its compatability with polyester resins, its good heat sealability (including sealing by RF methods), and its wide processing window and heat stability which allows extrusion processing at the elevated temperatures required for polyester extrusion (515–535 F.). EMA having a methyl acrylate content in the range of 18 to 20%, such as Emac SP2255 (18% methyl acrylate), Emac SP2242 (20% methyl acrylate), or Emac SP1257 (20% methyl acrylate), all available from Chevron Chemical Co. have been found particularly effective.

Although adequate interlayer adhesion is obtained with the skin layers 12, 13 in direct contact with the polyester barrier layer 11 (as depicted in FIG. 1), it is preferable to use an intermediate adhesive tie layer between the barrier layer and each skin layer for optimal interlayer adhesion. FIG. 2 illustrates a five-layer film in which the barrier layer 11' and skin layers 12' and 13' have the same compositions and thicknesses described above and in which tie layers 14, 15 are coextruded between the barrier and skin layers. The tie layers can be any of a number of ethylene copolymers suitable for use as adhesion promoters in coextrusion. Several resins suitable for use as tie layers are available commercially under the trademark "Bynel" (dupont Co.) and "Primacor" (Dow Chemical Co.). For a multilayer film with EMA skins, a suitable choice is anhydride-modified ethylene acrylate copolymer such as Bynel 2169, Bynel 2174 or Bynel 21E533 available from duPont Co.

FIG. 3 illustrates a typical ostomy pouch 16 having its walls 16a and 16b formed from the multilayer films of FIGS. 1 or 2. The films are arranged with their heat sealable skin layers facing each other and sealed together along the outer periphery of the pouch as indicated at 17. One wall of the pouch has a stoma-receiving opening 18 formed therein and an adhesive attachment ring 19 is located about that opening for adhesive attachment to the peristomal skin surfaces of a patient. The pouch as shown is the type generally referred to as a one-piece appliance but, if desired, a mechanical coupling ring may be substituted for adhesive ring 19, with the pouch therefore becoming one component of a two-piece ostomy appliance, all as well known in the art.

In order that the invention may be more readily understood, reference is made to the following examples which are intended to be illustrative of the invention, but are not intended to be limiting in scope.

EXAMPLE 1

A three-layer barrier film was produced in accordance with the present invention and included a core barrier layer and two outer skin layers joined directly to the core layer. The film was made by coextrusion casting at 535° F. and had a total thickness of 2.5 mil with a barrier layer thickness of 0.2 mil. The core barrier layer was a toughened grade of polyethylene terephthalate (Selar PTX184, duPont Co.) and each skin layer was a copolymer of ethylene and methyl acrylate having an 18% methyl acrylate content (EMAC SP2255, Chevron Chemical Co.).

For comparison purposes, a commercially-available multilayer film with a chlorinated barrier was selected as a control. The control film was composed of low density polyethylene coextruded with a barrier layer of polyvinylidene chloride.

The tensile moduli (psi) of the films were measured on an Instron tester (ASTM D882) with the secant modulus at 2% elongation being determined in both machine direction (MD) and transverse direction (TD). The results, tabulated in Table 1 below, reveals the film made in accordance with this invention to be considerably softer than the control film.

The lower modulus of the film having a polyester barrier layer was consistent with the results of quietness tests also tabulated below. Samples measuring approximately 4 inches by 4 inches of each film were formed into a cylinder and mounted on a test fixture wherein one end of the cylinder was held fixed and the other rotated around the cylinder's axis at an angle of 15°, 70 cycles/minute. Noise emissions produced by the film flexing were analyzed with a sound level meter. In the table, dBA is a weighted average that takes into account the human perception of noise over the entire frequency range, whereas dB values in the 8 and 16 kHz octave bands are indicative of the noise in the high frequency ranges and represent the crispness of the noise. The dBA and dB values in the 8 and 16 kHz octave bands therefore reveal that the film sample embodying the invention having a polyester core layer was considerably quieter than the control sample in which the core layer was PVDC.

TABLE 1

| Film | Tensile Modulus psi | | Noise | | |
| --- | --- | --- | --- | --- | --- |
| | MD | TD | dBA | dB, 8 kHz | dB, 16 kHz |
| EMA/Polyester/EMA | 24400 | 24800 | 64 | 49 | 42 |
| Prior art film with chlorinated barrier layer | 30000 | 31500 | 74 | 55 | 49 |

The samples were tested for odor transmission using British Standard 7127, Part 101, "Method for Determining Odor Transmission of Colostomy and Ileostomy Bag Materials," British Standard Institution, London, England. No odors were transmitted by the films. It is noteworthy that the odor barrier effectiveness of the film embodying this invention was achieved with a polyester barrier layer having a thickness of only 0.2 mil (in a total film thickness of 2.5 mil).

EXAMPLE 2

A three-layer barrier film in accordance with this invention was produced by coextrusion using conventional coextrusion casting techniques at 535° F., resulting in a multilayer film having a total thickness of 3 mil and a core barrier layer thickness of 0.2 mil. The composition of the barrier layer was toughened polyethylene terephthalate (Selar PTX184, duPont Co.) and skin layers of ethylene methyl acrylate copolymer with 20% methyl acrylate (EMAC SP1257, Chevron Chemical Co.).

Using the same procedure described in Example 1, the tensile moduli (psi) of the films were measured with the secant modulus at 2% elongation being determined in both machine direction and transverse direction. Noise emissions produced by the films were analyzed with a sound level meter in the same manner as described in Example 1. The comparative data appears in Table 2 below:

TABLE 2

| Film | Tensile Modulus psi | | Noise | | |
|---|---|---|---|---|---|
| | MD | TD | dBA | dB, 8 kHz | dB, 16 kHz |
| EMA/Polyester/EMA | 12960 | 14000 | 61 | 43 | 28 |

Tensile modulus and noise data reveal that a film embodying the invention having an EMA skin layer with a 20% methylacrylate content is even softer and quieter than the film of the previous example in which the methyl acrylate content of the EMA skin layer was 18%. As in the previous example, odor barrier effectiveness was achieved with a polyester barrier layer having a thickness of only 0.2 mil (no odor transmitted using the test method referenced above).

EXAMPLE 3

A five-layer barrier film was produced in accordance with this invention by coextrusion casting, resulting in a film with a total thickness of 3.5 mil and a barrier layer thickness of 0.3 mil. Unlike the films of the previous examples which utilize EMA resin as the skin layer, in this example the skin layer is based on polyethylene. Specifically, the film structure is A/B/C/B/A, wherein A is a polyethylene-based resin (2M042), Exxon Chemical Co.) modified by the addition of 5% of a slip/antiblock concentrate (EXT4226TSE, A. Schulman Co.) and 3% of a low density polyethylene (LD200.48, Exxon Chemical Co.); B is a tie layer consisting of anhydride-modified EMA (Bynel 21E533); and C is toughened polyethylene terephthalate (Selar PTX174, duPont Co.). The Bynel tie layer is particularly advantageous in this film structure to maximize adhesion to the polyethylene skin. Again, the tensile modulus at 2% elongation and the film noise were measured as described in the previous examples. The data is shown in Table 3 below:

TABLE 3

| Film | Tensile Modulus psi | | Noise | | |
|---|---|---|---|---|---|
| | MD | TD | dBA | dB, 8 kHz | dB, 16 kHz |
| PE/tie/Polyester/tie/PE | 25400 | 22800 | 65 | 40 | 30 |

Modulus and noise data indicate that the film of this example is noticeably softer and quieter than the commercial film reported in Example 1.

EXAMPLE 4

The barrier properties of the film of Example 3 were tested using three model compounds for fecal odor: dimethyldisulfide, indole and skatole. For comparison, the same test was conducted on a commercial ostomy film with chlorinated barrier. Analysis of effluent gases was conducted by gas chromatography using a flame ionization detector. The table below shows breakthrough times and concentration of each component in the effluent stream after 60 hrs.

TABLE 4

| Film | Breakthrough Times, min | | | Concentration at 60 hrs | | |
|---|---|---|---|---|---|---|
| | Dimethyl disulfide min | Indole min | Skatole min | Dimethyl disulfide ppm | Indole ppb | Skatole ppb |
| Film of Example 3 | 2280 | 1670 | 2180 | 29 | 140 | 38 |
| Control Film | 720 | 1140 | 1610 | 137 | 292 | 91 |

Better barrier properties are expected for films that show longer breakthrough times and lower effluent concentration. The film of Example 3 is superior to the chlorinated control in both respects, indicating superior performance as a barrier to fecal odorants.

While in the foregoing, embodiments of the invention have been disclosed in detail for purposes of illustration, it will be understood by those skilled in the art that many of these details may be varied without departing from the spirit and scope of the invention.

What is claimed is:

1. A multilayer heat sealable chlorine-free film comprising an odor barrier layer of coextrudable polyethylene terephthalate resin and two heat-sealable skin layers coextruded with said odor barrier layer and located on opposite sides thereof; said skin layers being composed of an ethylene polymer or copolymer with an alpha-olefin or an ester-containing monomer; said film having no more than five layers in total and including a coextruded intermediate adhesive tie layer of anhydride-modified ethylene acrylate copolymer between said odor barrier layer and each of said skin layers.

2. The multilayer film of claim 1 in which said barrier layer has a thickness of about 0.1 to 0.4 mil and each skin layer has a thickness of about 0.5 to 2 mil.

3. The multilayer film of claim 1 in which said skin layers consist essentially of a copolymer of ethylene and an ester-containing comonomer selected from the group consisting of methyl acrylate, ethyl acrylate, butyl acrylate and vinyl acetate.

4. The multilayer film of claim 3 in which said skin layers are composed essentially of a copolymer of ethylene and methyl acrylate having a methyl acrylate content in the range of about 10% to 30% by weight.

5. The multilayer film of claim 1 in which said film exhibits a noise of less than about 50 dB in the 8 kHz and 15 kHz octave bands, respectively, when subjected to flexing through a 15° angle at 70 cycles/minute.

6. An ostomy pouch having two side walls each being formed of a multilayer chlorine-free film having an odor barrier layer coextruded with two heat-sealable skin layers on opposite sides of said odor barrier layer; said skin layers of said walls facing each other and being heat sealed together along peripheral edge portions of said pouch; said odor barrier layers of said walls being composed of coextrudable polyethylene terephthalate resin and said skin layers comprising an ethylene polymer or copolymer with an alpha-olefin or ester-containing monomer; each of said walls having no more than five layers in total and including a coextruded intermediate adhesive tie layer of anhydride-modified ethylene acrylate copolymer between said odor barrier layer and each of said skin layers.

7. The ostomy pouch of claim 6 in which said barrier layer has a thickness of about 0.1 to 0.4 mil and each skin layer has a thickness of about 0.5 to 2 mil.

8. The ostomy pouch of claim 6 in which said skin layers consist essentially of a copolymer of ethylene and an ester-containing comonomer selected from the group consisting of methyl acrylate, ethyl acrylate, butyl acrylate and vinyl acetate.

9. The ostomy pouch of claim 6 in which said skin layers are composed essentially of a copolymer of ethylene and methyl acrylate having a methyl acrylate content in the range of about 10% to 30% by weight.

10. The ostomy pouch of claim 6 in which said film exhibits a noise of less than about 50 dB in the 8 kHz and 16 kHz octave bands, respectively, when subjected to flexing through a 15° angle at 70 cycles/minute.

* * * * *